(12) United States Patent
Yener et al.

(10) Patent No.: US 11,197,966 B2
(45) Date of Patent: Dec. 14, 2021

(54) ELECTRONIC VAPING DEVICE WITH FLOATING ATOMIZER

(71) Applicant: Fontem Holdings 1 B.V., Amsterdam (NL)

(72) Inventors: Emin Yener, Hamburg (DE); Vaclav Borkovec, Hamburg (DE)

(73) Assignee: Fontem Holdings 1 B.V., Amsterdam (NL)

(*) Notice: Subject to any disclaimer, the term of this patent is extended or adjusted under 35 U.S.C. 154(b) by 624 days.

(21) Appl. No.: 15/765,234

(22) PCT Filed: Sep. 30, 2016

(86) PCT No.: PCT/EP2016/073442
§ 371 (c)(1),
(2) Date: Mar. 30, 2018

(87) PCT Pub. No.: WO2017/055564
PCT Pub. Date: Apr. 6, 2017

(65) Prior Publication Data
US 2018/0296776 A1  Oct. 18, 2018

(30) Foreign Application Priority Data
Oct. 1, 2015 (EP) .................................... 15187855

(51) Int. Cl.
*A61M 11/04* (2006.01)
*A24F 1/30* (2006.01)
(Continued)

(52) U.S. Cl.
CPC ............. *A61M 11/042* (2014.02); *A24F 1/30* (2013.01); *A24F 40/42* (2020.01); *A24F 40/46* (2020.01); *A61M 11/006* (2014.02); *A61M 15/06* (2013.01); *A24F 40/10* (2020.01); *A61M 11/005* (2013.01); *A61M 11/02* (2013.01);
(Continued)

(58) Field of Classification Search
CPC .... A61M 11/042; A61M 15/06; A61M 11/06; A61M 11/005; A61M 15/0085; A61M 11/045; A24F 1/30; A24F 47/008; A24F 40/10; A24F 40/46; A24F 40/40
See application file for complete search history.

(56) References Cited

U.S. PATENT DOCUMENTS 3,398,897 A * 8/1968 Urbanowicz .......... A61M 11/06
239/338
5,297,734 A * 3/1994 Toda .................... B05B 17/0646
239/102.2
(Continued)

FOREIGN PATENT DOCUMENTS

GB       1346024 A    2/1974
JP      H07213968 A    8/1995
(Continued)

*Primary Examiner* — Margaret M Luarca
(74) *Attorney, Agent, or Firm* — Dykema Gossett PLLC

(57) ABSTRACT

An electronic vaping device is provided including a power supply portion comprising a power supply, an atomizer/liquid reservoir portion comprising a liquid reservoir storing a liquid, and an atomizer adapted to atomize the liquid stored in the liquid reservoir when operated by the power supply. The atomizer is adapted to float on the surface of the liquid in the liquid reservoir.

5 Claims, 7 Drawing Sheets

(51) Int. Cl.
  *A61M 15/06* (2006.01)
  *A61M 11/00* (2006.01)
  *A24F 40/42* (2020.01)
  *A24F 40/46* (2020.01)
  *A61M 11/02* (2006.01)
  *A61M 15/00* (2006.01)
  *A61M 16/00* (2006.01)
  *A61M 11/06* (2006.01)
  *A24F 40/10* (2020.01)

(52) U.S. Cl.
  CPC ......... *A61M 11/06* (2013.01); *A61M 15/0085* (2013.01); *A61M 2016/0021* (2013.01); *A61M 2016/0024* (2013.01); *A61M 2016/0027* (2013.01); *A61M 2016/0039* (2013.01); *A61M 2205/3653* (2013.01); *A61M 2205/8212* (2013.01); *A61M 2205/84* (2013.01)

(56) References Cited

U.S. PATENT DOCUMENTS

2006/0201501 A1   9/2006   Morrison et al.
2007/0169775 A1   7/2007   Chen et al.
2009/0320840 A1*  12/2009  Klasek ................ A61M 16/108
                                                 128/203.27

FOREIGN PATENT DOCUMENTS

WO    2005079898 A2   9/2005
WO    2008055307 A1   5/2008
WO    2013060743 A2   5/2013

\* cited by examiner

ELECTRONIC VAPING DEVICE WITH FLOATING ATOMIZER

FIELD OF INVENTION

The present invention relates generally to electronic vaping devices.

BACKGROUND OF THE INVENTION

An electronic vaping device, such as an electronic shisha, typically has a housing accommodating an electric power source (e.g. a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic vaping devices, an airflow sensor is provided within the electronic vaping device, which detects a user puffing on the device (e.g., by sensing an under-pressure or an air flow pattern through the device). The airflow sensor indicates or signals the puff to the control electronics to power up the device and generate vapor. In other e-vaping devices, a switch or push button is used to power up the e-vaping device to generate a puff of vapor.

In order to ensure constant operability of the electronic vaping device, the atomizer has to be reliably supplied with liquid to be vaporized.

SUMMARY OF THE INVENTION

In accordance with one aspect of the present invention there is provided an electronic vaping device including a power supply portion and an atomizer/liquid reservoir portion. The power supply portion comprises a power supply. The atomizer/liquid reservoir portion comprises a liquid reservoir storing a liquid, and an atomizer adapted to atomize the liquid stored in the liquid reservoir when operated by the power supply. The atomizer is adapted to float on the surface of the liquid in the liquid reservoir.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Figure 1:
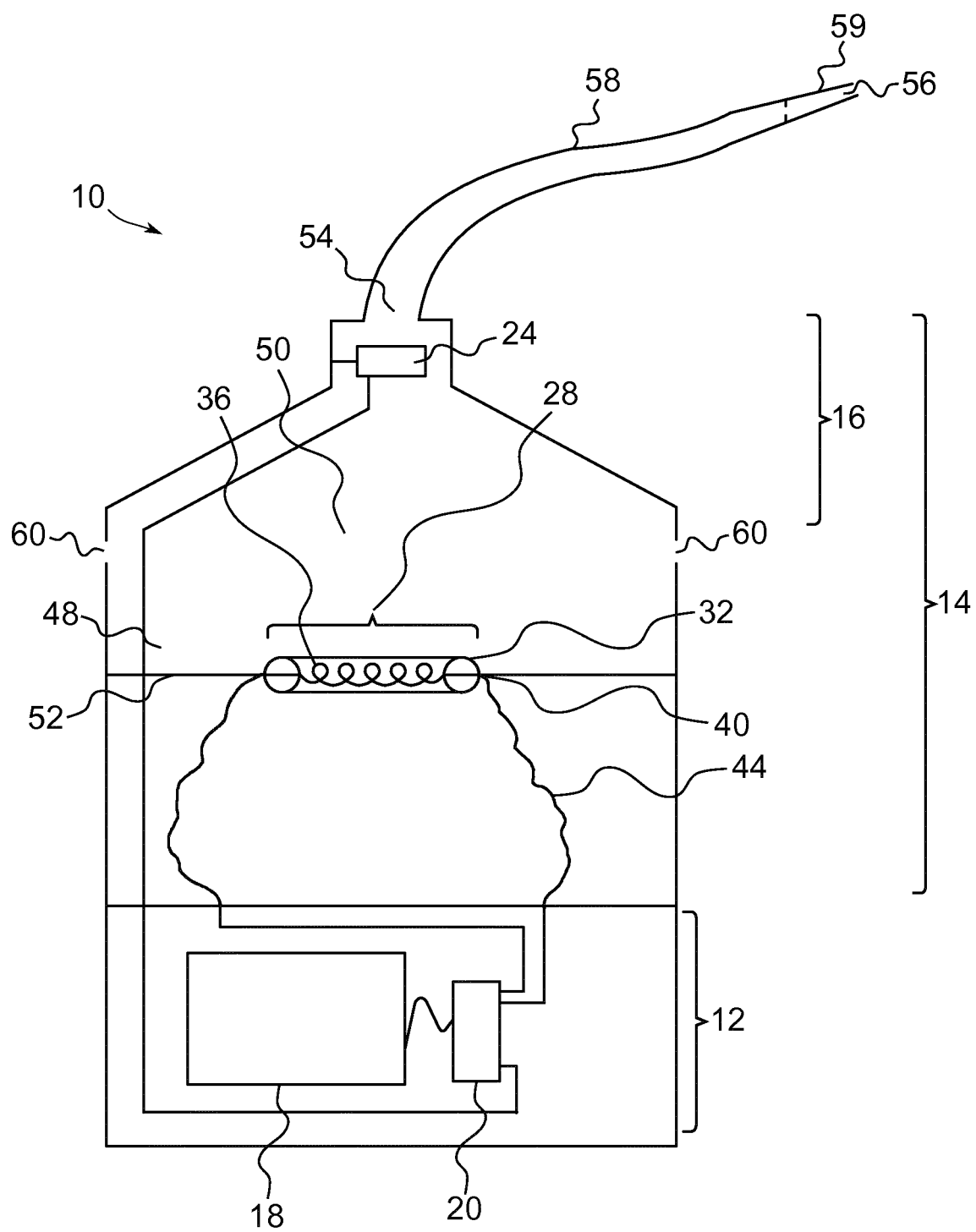
FIG. 1 is a schematic cross-sectional illustration of an exemplary electronic vaping device.

Throughout the following, an electronic vaping device 10 will be exemplarily described with reference to an e-shisha. However, the electronic vaping device 10 can be any electronic inhalation device which vaporizes a liquid. As is shown in FIG. 1, an electronic vaping device typically has a housing comprising a cylindrical hollow tube having a tapering top portion 16. The cylindrical hollow tube may be a single-piece or a multiple-piece tube. In FIG. 1, the cylindrical hollow tube is shown as a two-piece structure having a power supply portion 12 as one piece and an atomizer/liquid reservoir portion 14 together with the tapering end portion 16 as the second piece.

The tapering end portion 16 may also be provided as a separate piece, having varying geometrical shapes, e.g. hemispherical. The power supply portion 12 may be provided in the end portion 16. The size of the housing as well as the specific geometry of the hollow tube portion may also vary. Typically, the housing has a diameter of about 50 to 200 mm and a total height of about 150 to 500 mm.

The power supply portion 12 and atomizer/liquid reservoir portion 14 are typically made of metal, e.g. steel or aluminum, ceramic, glass, or of hardwearing plastic and act together with the tapering end portion 16 to provide a housing to contain the components of the electronic vaping device 10. The power supply portion 12 and an atomizer/liquid reservoir portion 14 may be configured to fit together by a friction push fit, a snap fit, or a bayonet attachment, magnetic fit, or screw threads.

A battery 18 and control electronics 20 are provided within the cylindrical hollow tube power supply portion 12. An optional airflow sensor 24 is provided in the housing, in the vicinity of an opening 54 at the top end of the tapering end portion 16. The battery 18 is electrically connected to the control electronics 22, which are electrically connected to the airflow sensor 24.

The airflow sensor 24 acts as a puff detector, detecting a user puffing or sucking on a mouthpiece 59 of a flexible tube 58 that is arranged at the top end of the atomizer/liquid reservoir portion 14 of the electronic vaping device 10. By means of the flexible tube 58, an air inhalation port 56 for the user is provided. A suitable air inhalation port 56 can also be provided directly at the opening 54, i.e. the flexible tube 58 is optional. The airflow sensor 24 can be any suitable sensor for detecting changes in airflow or air pressure, such as a microphone switch including a deformable membrane which is caused to move by variations in air pressure. Alternatively the sensor may be a Hall element or an electro-mechanical sensor.

The control electronics 20 are also connected to an atomizer 28. In the example shown in FIG. 1, a contact-type connection is provided between the control electronics 20 and the atomizer 28, namely via flexible conductive wires 40, which contact the atomizer 28 at respective contact ports 40. Alternatively, a connection between the control electronics 20 and the atomizer 28 may be of a non-contact-type, e.g. by inductive coupling.

Figure 2A:
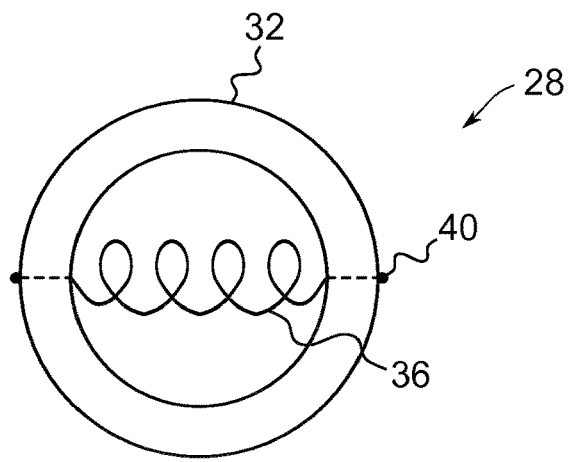
FIG. 2A is a top view of an atomizer according to a first embodiment.

In the example shown in FIG. 1, the atomizer 28, which is wickless, includes a heating wire 36 extending essentially along a diameter of a ring-like floating element 32 (a top view of the atomizer 28 is shown in FIG. 2A). The floating element 32 is adapted to float on the surface 52 of the liquid provided in the liquid reservoir 48 of the atomizer/liquid reservoir portion 14. The heating wire 36 is supported by the floating element 32 so that, when the floating element 32 floats on the liquid surface 52, the heating wire 36 is in contact with the liquid in the liquid reservoir 48. In addition, according to this arrangement the heating wire 36 is close to a vaping chamber 50 above the liquid surface 52. Therefore, aerosol generated by operating the heating wire 36 does not get cooled so fast compared to an arrangement in which the heating wire 36 is arranged deep under the liquid surface 52. As a consequence, according to the present arrangement including the floating atomizer 28, more vapor can be generated with less energy required.

The atomizer 28 may alternatively use other forms of heating elements 36, such as ceramic heaters, or fiber or mesh material heaters. Nonresistance heating elements such as sonic, piezo and jet spray may also be used in the atomizer in place of the heating coil.

As already indicated above, an air inhalation port 56 is provided at the end of a flexible tube 58 that is connected to the top end of the atomizer/liquid reservoir portion 14 in the area of the opening 54.

In use, a user sucks on the electronic vaping device 10, i.e. on the air inhalation port 56. This causes air to be drawn into the electronic vaping device 10 via one or more air inlets, such as air inlets 60 provided in the side wall of the atomizer/liquid reservoir portion 14, and to be drawn through the vaping chamber 50 towards the air inhalation port 56. The change in air pressure which arises is detected by the airflow sensor 24, which generates an electrical signal that is passed to the control electronics 20. In response to the signal, the control electronics 20 activate the heating wire 36, which causes liquid present around the heating wire 36 to be vaporized creating an aerosol (which may comprise gaseous and liquid components) within the vaping chamber 50. As the user continues to suck on the mouthpiece 59 of the electronic vaping device 10, this aerosol is drawn through the flexible tube 58 and inhaled by the user. Due to the fact that the atomizer 28 floats on the surface of the liquid in the liquid reservoir 48 so that the heating wire 36 is in contact with the liquid in the liquid reservoir, liquid is constantly available to be converted into an aerosol through subsequent activation of the heating wire 36.

Typically, the battery 18 is rechargeable and the liquid reservoir 48 is refillable. In other embodiments the atomizer/liquid reservoir portion 14 of the electronic vaping device 10 is detachable from the power supply portion 12 and a new atomizer/liquid reservoir portion 14 can be fitted with a new liquid reservoir 48 thereby replenishing the supply of liquid. In some cases, replacing the liquid reservoir 48 may involve replacement of the atomizer 28 along with the replacement of the liquid reservoir 48. According to a preferred embodiment, the atomizer 28 is provided separate from the liquid reservoir 48 and is replaced if required, independent of refill or replacement of the liquid reservoir 48.

Of course, in addition to the above description of the structure and function of a typical electronic vaping device 10, variations also exist. The airflow sensor 24 may be placed somewhere inside the vapor chamber 50, e.g. in the vicinity of the air inlets 60. The airflow sensor 24 may be replaced with a switch or push button which enables a user to activate the electronic vaping device manually rather than in response to the detection of a change in air flow or air pressure.

Different types of atomizers may be used, as described in detail with reference to FIG. 2A to 2E below.

In FIG. 2A, the atomizer 28 of FIG. 1 is illustrated in top view. The atomizer 28 comprises a floating element 32 that is ring-shaped or torus-shaped. The floating element 32 is adapted to float on the surface 52 of the liquid provided in a liquid reservoir 48 of an electronic vaping device 10, such as the electronic vaping device of FIG. 1. Any suitable material can be used to form the floating element 32, as long as respective functionalities are provided, such as a suitably relative density, and sufficient resistance with respect to humidity and heat.

The floating element 32 supports a heating element 36, which is shown in FIG. 2A in the form of a heating wire 36. The heating wire 36 extends essentially along a diameter of the ring-shaped floating element 32. The arrangement of the heating element 36 with respect to the floating element is such that the heating element 36 is in contact with liquid when the floating element floats on the surface 52 of liquid provided in a liquid reservoir 48.

The heating wire 36 can be electrically contacted via the contact ports 40 at the outer surface of the floating element 32 through which the ends of the heating wire 36 extend (as indicated by the dotted lines in FIG. 2A). The geometric form of the floating element 32 can vary, the floating element can e.g. be U-shaped or L-shaped and the heating wire 36 can extend between the respective legs of the U or L.

Figure 2B:
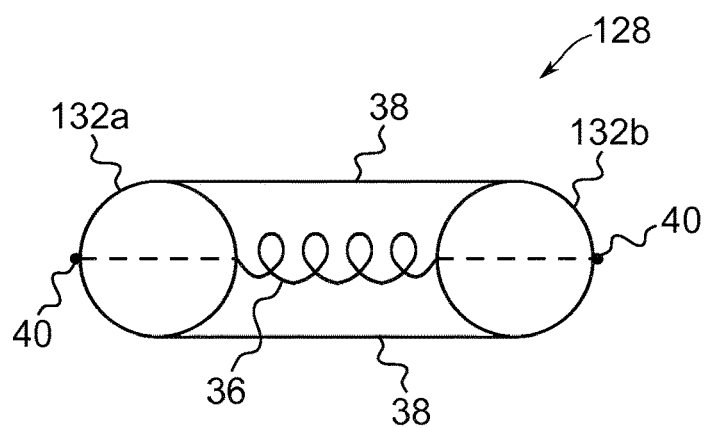
FIG. 2B is a top view of an atomizer according to a second embodiment.

As shown in FIG. 2B, which illustrates a second embodiment of an atomizer 128 in top view, also a plurality of floating elements 132a, 132b can be provided in order to build an atomizer 128. The two floating elements 132a, 132b are connected and kept separated by suitable distance elements 38. The floating elements 132a, 132b are ball-shaped. Different geometrical forms, such as cuboids or the like, are possible. Also the number of floating elements used to form a floating atomizer may vary. The heating wire 36 extends between the two floating elements 132a, 132b and can again be electrically contacted to respective control electronics via respective contact ports 40. The overall arrangement of the atomizer 128 of FIG. 2B is such that the heating wire 36 is in contact with liquid of a liquid reservoir 48 when the atomizer 128, by means of the floating elements 132a, 132b, floats on the respective liquid surface 52.

Figure 2C:
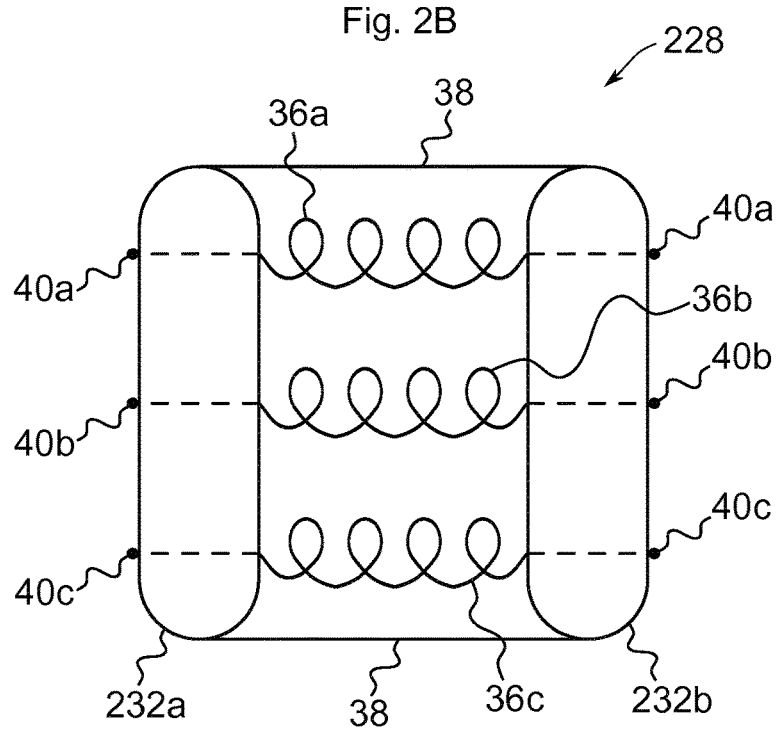
FIG. 2C is a top view of an atomizer according to a third embodiment.

In FIG. 2C, a third embodiment of an atomizer 228 is illustrated in top view. In contrast to the atomizer 128 of FIG. 2B, the floating elements 232a, 232b have an elongate shape and a plurality of heating wires, in the specific example three heating wires 36a, 36b, 36c, extend between the floating elements 232a, 232b. Each of these heating wires 36a, 36b, 36c, can separately be contacted via respective contacts ports 40a, 40b, 40c.

Figure 2D:
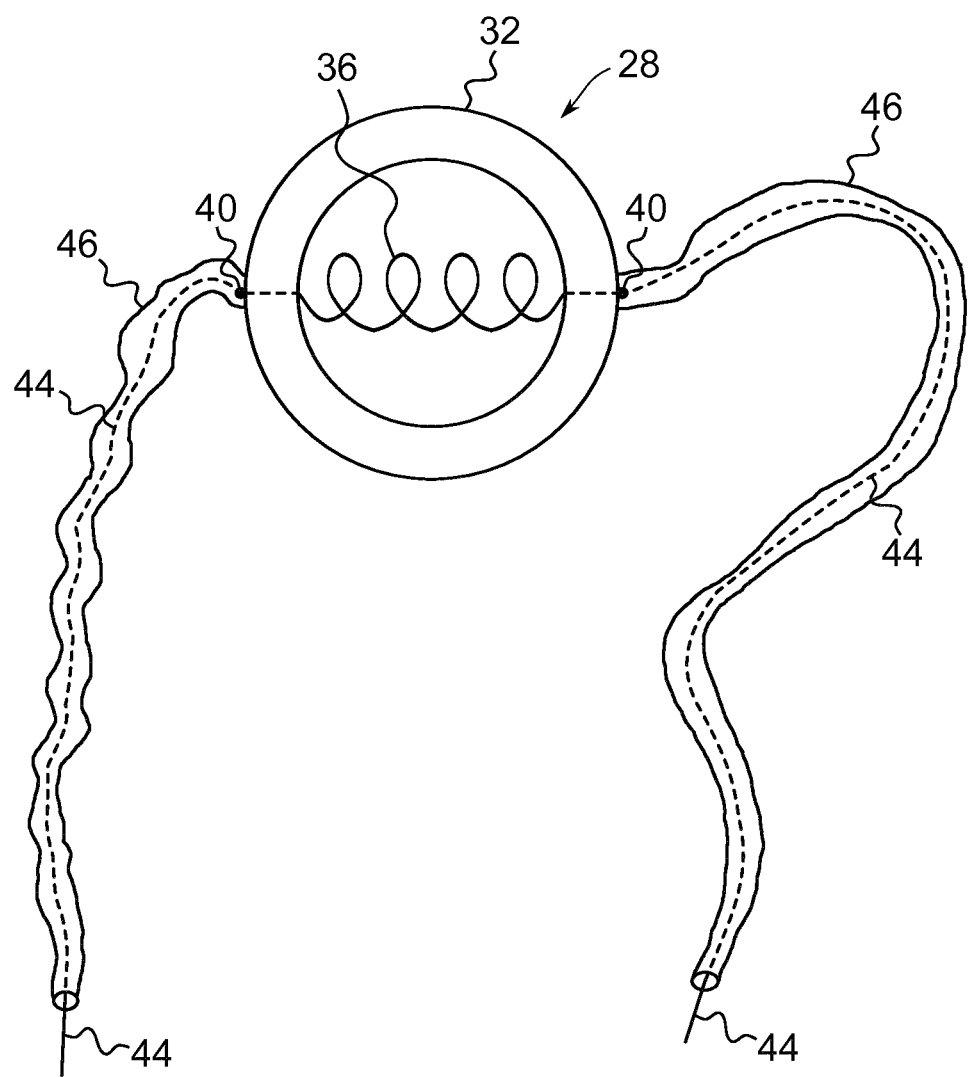
FIG. 2D is a top view of a variant of the atomizer of FIG. 2A.

In FIG. 2D, a variant of the atomizer 28 of FIG. 2A is shown in plan view. Floating tubes 46 are directly connected to the atomizer 28 in the area of the contact ports 40. The tubes 46 are adapted to enclose the flexible conductive wires 44 via which the atomizer 28 can be connected to a power source 18. Due to the fact that the tubes 46 are adapted to also float on the surface 52 of the liquid, together with the atomizer 28, a contact to a power source 18 that, in contrast to the arrangement shown in FIG. 1, is provided at a side wall of the liquid reservoir 48 can easily be provided. The tubes 46 can move up and down on the surface of the liquid.

Figure 2E:
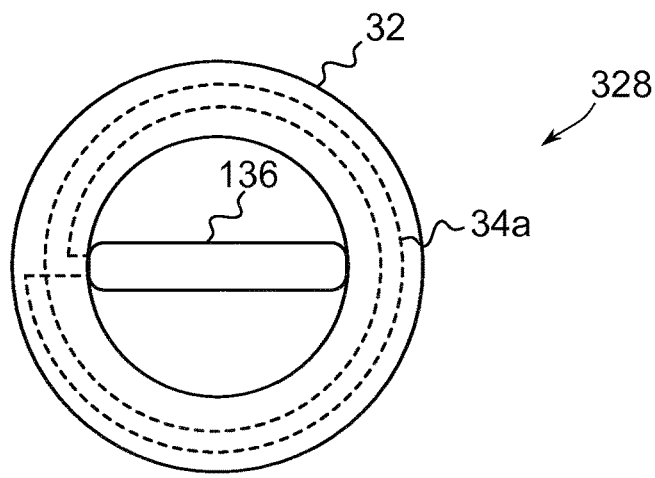
FIG. 2E is a top view of an atomizer according to a fourth embodiment.

In FIG. 2E, another variant of an atomizer 328 is illustrated in top view. The atomizer 328, in order to be operated by the power supply 18, is adapted to be connected to the power supply 18 by means of a noncontact-type connection, namely via inductive coupling. To that end, an antenna coil 34a is integrated into the floating element 32, as indicated by the dotted line in FIG. 2E. In contrast to the embodiment shown in FIG. 2A, the atomizer 328 comprises a heating element 136 in the form of a ceramic heater. However, any other heating element 136 that is configured to be operated by inductive coupling can be used.

Figure 2F:
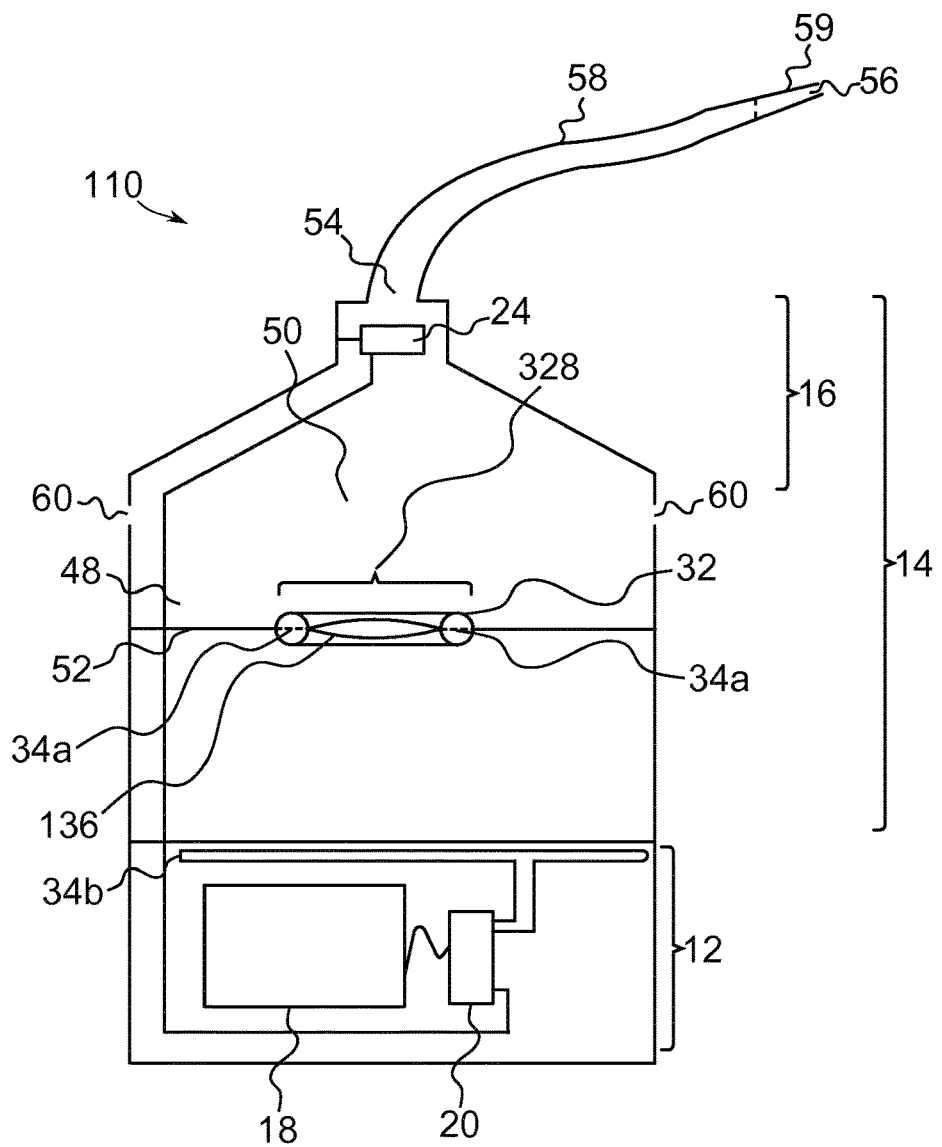
FIG. 2F is a cross-sectional illustration of an electronic vaping device according to a second embodiment.

A respectively configured electronic vaping device 110 according to a second embodiment is illustrated in a cross-sectional view in FIG. 2F. The electronic vaping device 110 in FIG. 2F essentially equals the electronic vaping device 10 according to FIG. 1. In order to contact the atomizer 328 inductively, an antenna coil 34b is provided, which is connected to the control electronics 20, instead of the conductive wire 44 shown in FIG. 1.

Figure 2G:
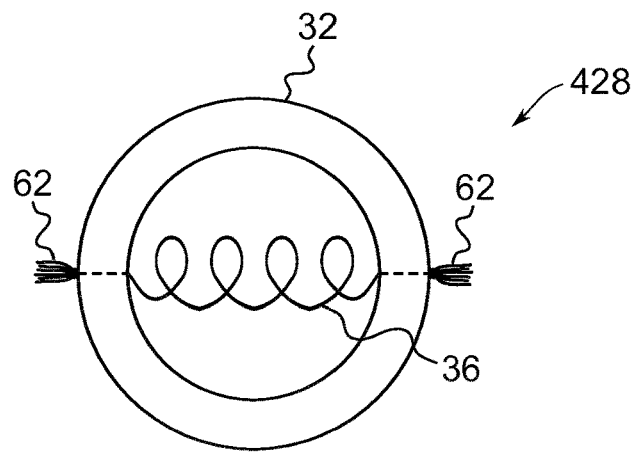
FIG. 2G is a top view of an atomizer according to a fifth embodiment.
Figure 2H:
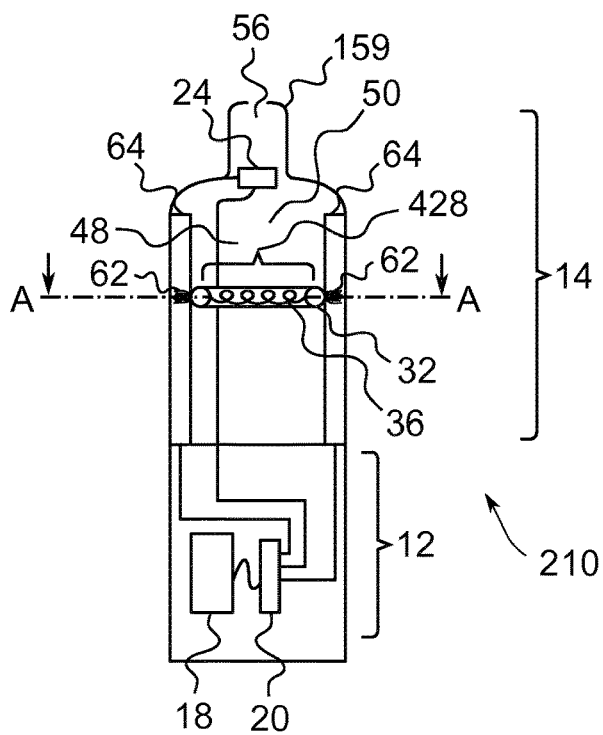
FIGS. 2H and 2I illustrate a third embodiment of an electronic vaping device in a cross-sectional front view and a cross-sectional top view.
Figure 2I:
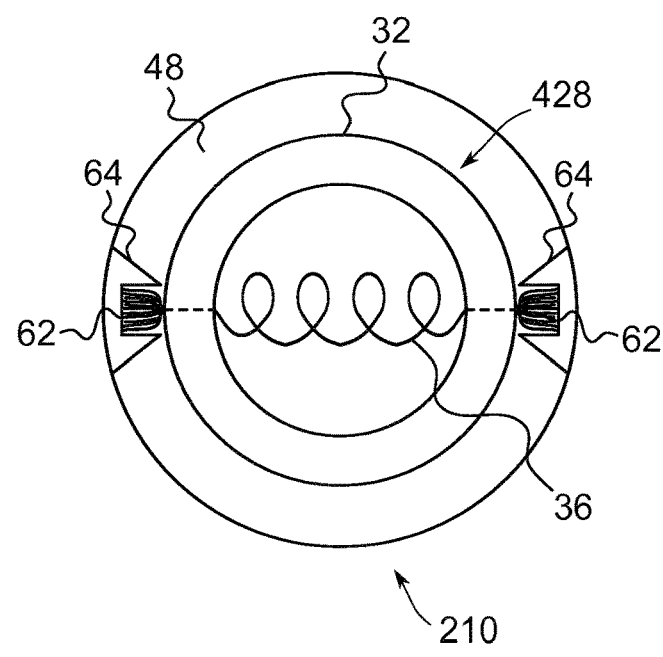
Figure 2J:
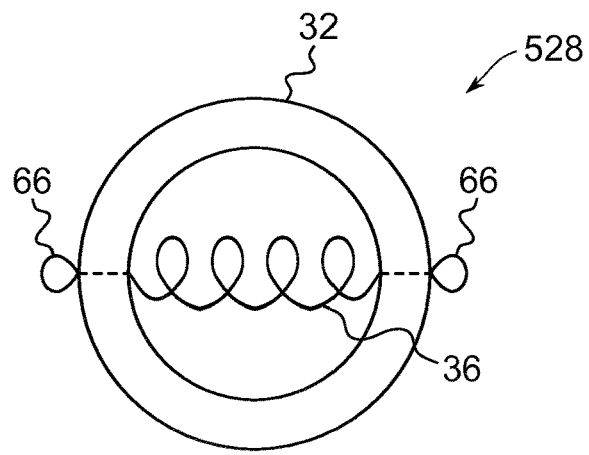
FIG. 2J is a top view of an atomizer according to a sixth embodiment.

In FIGS. 2G and 2J, further variants of atomizers 428, 528 are illustrated in top view. These atomizers 428, 528, in order to be operated by the power supply 18, are again adapted to be connected to the power supply 18 by means of a contact-type connection. However, in contrast to the embodiment according to FIGS. 1 and 2, where the atomizer 28 is connected to the power supply 18 by means of the conductive wires 44 that are permanently and fixedly connecting the atomizer 28 to the power supply 18, the contact-type connection of the atomizers 428, 528 to the power supply 18 is rather loose. In order to establish a respective loose conductive connection between the atomizer 428, 528 and the power supply 18, the atomizers 428, 528 include conductive contacting elements 62, 66 on an outer surface. The contacting elements 62, 66 are configured, when the respective atomizer 428, 528 floats on the liquid surface 52, to be guided by conductive guiding elements 64, 68 that are provided in the liquid reservoir 48 and that are conductively connected to the power supply 18. The contacting elements 62, 66, while being guided by the guiding elements 64, 68, are loosely conductively connected to the guiding elements, and thus to the power supply 18.

As show in FIG. 2G with respect to the atomizer 428, the conductive contacting elements can e.g. be provided in the form of conductive wire brushes 62. Such wire brushes 62 are configured to be guided by conductive guiding elements in the form of conductive guiding troughs 62, as described below with respect to FIGS. 2H and 2I.

Alternatively, as shown in FIG. 2J with respect to the atomizer 528, the conductive contacting elements can e.g. be provided in the form of conductive loops 66. Such loops 66 are configured to be guided by conductive guiding elements in the form of conductive guide wires 68, as described below with respect to FIGS. 2K and 2L.

Embodiments of vaping devices 210, 310 that are adapted to include atomizers 428, 528 of the above described type are illustrated in FIGS. 2H, 2I and 2K, 2L. The respective vaping devices 210, 310 are intended to be used by a single user. The geometry of the vaping devices 210, 310, which is essentially rod-shaped, slightly differs from the geometry of the vaping devices 10, 110 in FIG. 1, 2F, because the vaping devices 210, 310 are intended to be used one-handedly, i.e. by only using a single hand. There is no flexible tube 58 at the top end of the atomizer/liquid reservoir portion 14, where a respective mouthpiece 159 providing an inhalation port 56 is directly located. This design choice, however, does not influence the general function of the respective electronic vaping devices 210, 310 when a user puffs on the vaping device, which function has already been described in detail with respect to FIG. 1.

FIGS. 2H and 2I illustrate an embodiment of a vaping device 210 in a cross-sectional front view (FIG. 2H) and in a cross-sectional top view (FIG. 2I; with respect to line A-A in FIG. 2H), which includes the atomizer 428 according to FIG. 2G. In the liquid reservoir 48, at opposing inner surfaces, conductive guide troughs 64 extending along the longitudinal direction of the liquid reservoir 48 are provided, which are connected to the power supply 18. The atomizer 428, while floating on the surface of the liquid in the liquid reservoir 48, loosely contacts the conductive guide troughs 64 by means of the wire brushes 62, irrespective of the current level of the fluid, as illustrated in FIG. 2H.

Figure 2K:
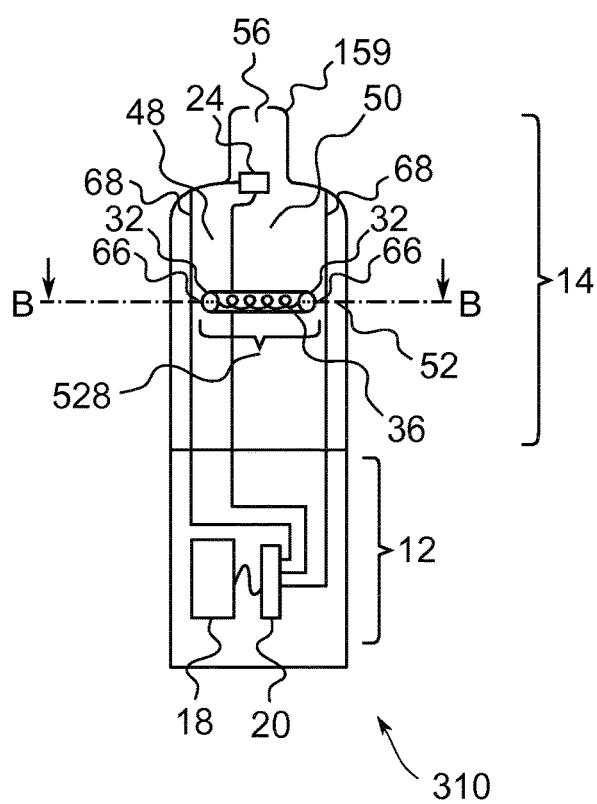
FIGS. 2K and 2L illustrate a fourth embodiment of an electronic vaping device in a cross-sectional front view and a cross-sectional top view.
Figure 2L:
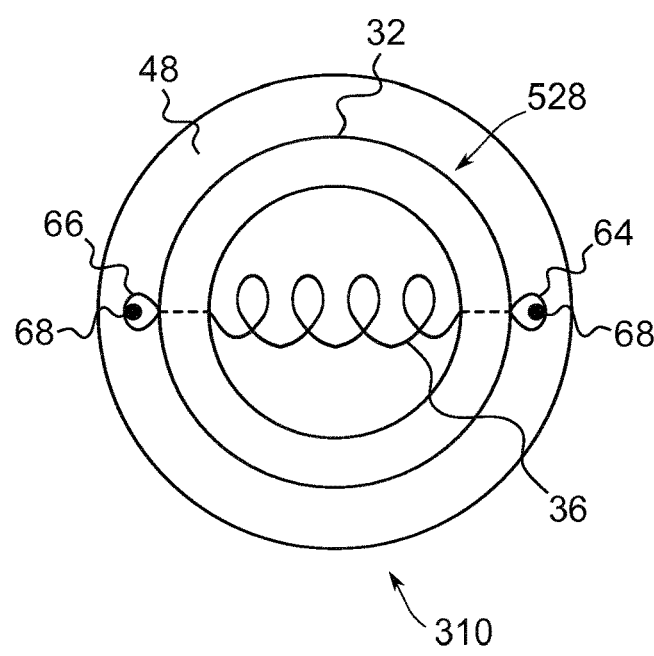

FIGS. 2K and 2L illustrate an embodiment of a vaping device 310 in a cross-sectional front view (FIG. 2K) and in a cross-sectional top view (FIG. 2L; with respect to line B-B in FIG. 2K), which includes the atomizer 528 according to FIG. 2J. In the liquid reservoir 48, at opposing sides, conductive guide wires 68 extending along the longitudinal direction of the liquid reservoir 48 are provided, which are connected to the power supply 18. The atomizer 528, while floating on the surface 52 of the liquid in the liquid reservoir 48 and irrespective of the current level of the fluid, loosely contacts the conductive guide wires 68 by means of the conductive loops 66, as illustrated in FIG. 2L.

The number of the contacting elements and the specific position on the surface of the atomizer at which the contacting elements are located may vary, with corresponding variations with respect to the number and position of the guiding elements in the liquid reservoir of the electronic vaping device, as long as the above described concept of a loose conductive coupling of the atomizer to the power supply can be ensured.

While the electronic vaping device 10 according to FIG. 1 is intended to be used by a single user, electronic vaping devices that can simultaneously be used by multiple users can be provided. An exemplary embodiment of such a multi-user electronic vaping device 410 is illustrated in a cross-sectional view in FIG. 3.

Figure 3:
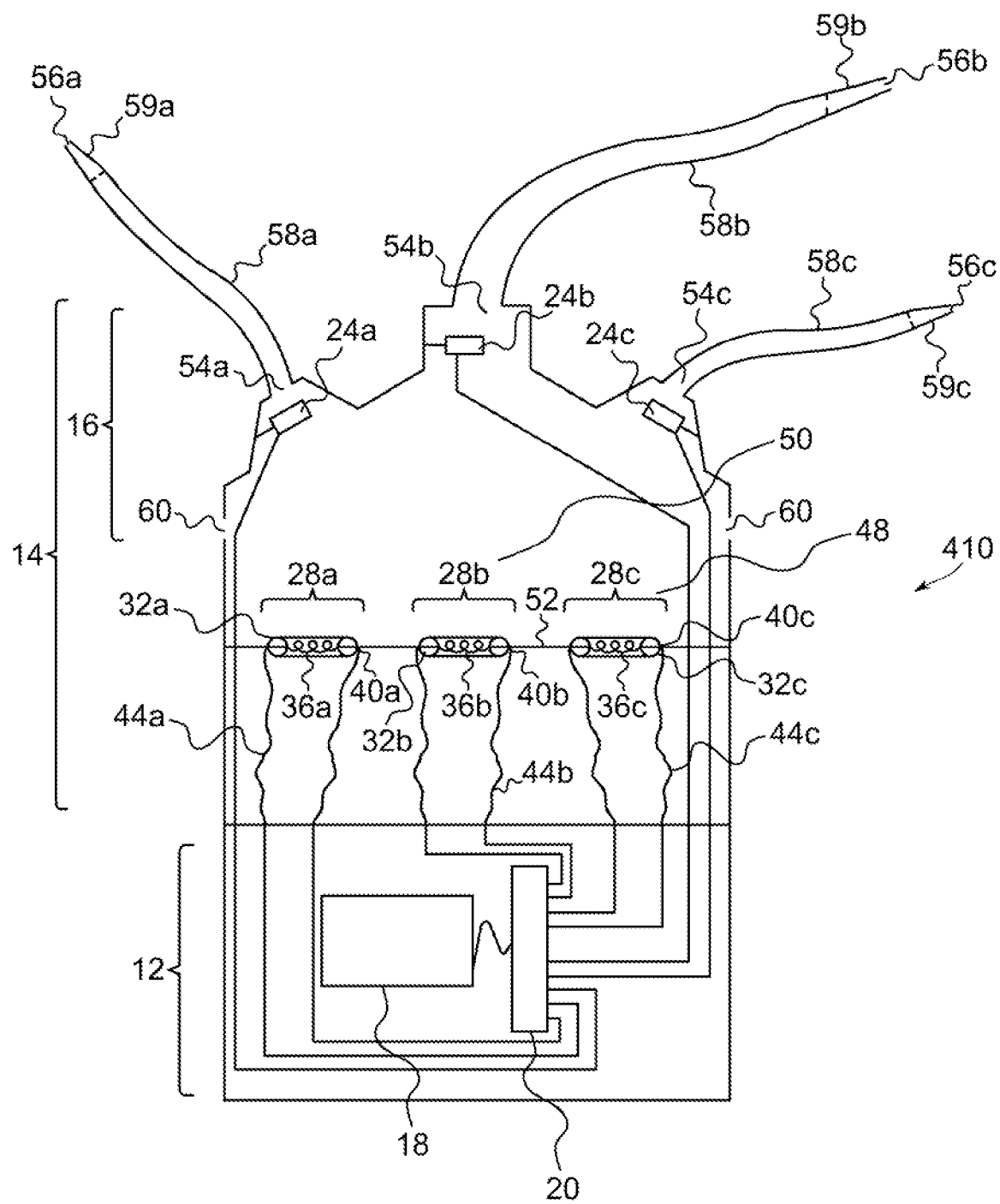
FIG. 3 is a schematic cross-sectional illustration of an electronic vaping device according to a fifth embodiment.

In contrast to the electronic vaping device 10 of FIG. 1, according to FIG. 3 three inhalations ports 56a, 56b, 56c are provided in the tapering top end portion 16 so that three users can simultaneously use the electronic vaping device 410. In the vicinity of the respective openings 54a, 54b, 54c of the top portion 16 of the atomizer/liquid reservoir portion 14, at which openings 54a, 54b, 54c the respective flexible tubes 58a, 58b, 58c with mouthpieces 59a, 59b, 59c are arranged, respective airflow sensors 24a, 24b, 24c are provided. According to the specific local arrangement of the airflow sensors 24a, 24b, 24c, it can not only be detected by the air flow sensors 24a, 24b, 24c that a users puffs at an inhalation port, but it can be detected at which inhalation port 56a, 56b, 56c a respective user puffs or at which of the inhalation ports 56a, 56b, 56c multiple users simultaneously puff. In other words, to each inhalation port 56a, 56b, 56c a respective airflow sensor 24a, 24b, 24c is assigned, which is arranged in the vaping chamber so as to detect a user puffing at the respectively assigned inhalation port 56a, 56b, 56c.

Further, in contrast to the electronic vaping device 10 shown in FIG. 1, according to FIG. 3 multiple atomizers 28a, 28b, 28c are provided in the liquid reservoir 48. Each of these atomizers 28a, 28b, 28c equals the atomizer 28 shown in FIG. 2A and is separately connected to the control electronics 20 by respective conductive wires 44a, 44b, 44c. The control electronics 20 are adapted to separately and selectively operate each of the atomizers 28a, 28b, 28c, one after another or simultaneously, as required.

To each of the inhalations ports 56a, 56b, 56c one of the atomizers 28a, 28b, 28c is respectively assigned. In case e.g. the airflow sensor 24a, which is assigned to the inhalation port 56a, detects a user puffing at this inhalation port 56a, the control electronics 20, based on a respective puff signal received from the airflow sensor 24a, operates the atomizer 24a, which is assigned to the inhalation port 56a, in order to generate an aerosol. Analogously, users puffing at the other inhalation ports 56b, 56c cause the control electronics 20 to operate the respectively assigned atomizers 28b, 28c, based on puffing signals received by the airflow sensors 28b, 28c. E.g. in case that three users simultaneously puff at the inhalation ports 56a 56b, 56c, all three atomizers 28a, 28b, 28c are operated simultaneously by the control electronics. In other words, each of the atomizers 28a, 28b, 28c is assigned to one of the potential multiple users and is adapted to be operated when the respectively assigned user uses the electronic vaping device 410.

As already mentioned above with respect to FIG. 1, also in the context of this embodiment, respective switches or push buttons can be used, instead of the air flow sensors 24a, 24b, 24c, in order to power up the respective atomizers 28a, 28b, 28c. In this case, one switch or push button would be assigned to each of the atomizers 28a, 28b, 28b, respectively.

According to an alternative embodiment (not shown in the figures), instead of the three atomizers 28a, 28b, 28c, one atomizer 228 according to FIG. 2C can be used in the electronic vaping device 410. Each of the heating wires 36a, 36b, 36c is then connected to the control electronics 20 by separate conductive wires 44a, 44b, 44c. The control electronics 20 are then adapted to separately and selectively operate each of the heating wires 36a, 36b, 36c of the atomizer 228. It is apparent that a multi-user usage can be handled with respect to such an embodiment just as described above with respect to FIG. 3. In other words, the atomizer 228 can be operated depending on the number of users that simultaneously use the electronic vaping device.

The atomizer 228 according to FIG. 2C, further to the usage in a multi-user setting as just described, can advantageously also be used in a single-user setting. In case an airflow sensor 24 is adapted to not only detect that a users puffs at an inhalation port, but also to detect the duration and/or the intensity of the puff, by means of the atomizer 228 more or less vapor can be generated by simultaneously operating more than one of the heating wires 36a, 36b, 36c or by operating just one of the heating wires 36a, 36b, 36c.

In summary, in one aspect an electronic vaping device includes a power supply portion comprising a power supply, an atomizer/liquid reservoir portion comprising a liquid reservoir storing a liquid, and an atomizer adapted to atomize the liquid stored in the liquid reservoir when operated by the power supply. The atomizer is adapted to float on the surface of the liquid in the liquid reservoir.

According to an embodiment, the atomizer comprises a floating element that is adapted to float on the liquid surface and a heating element that is supported by the floating element so that the heating element is in contact with the liquid when the floating element floats on the liquid surface.

According to an embodiment, the heating element comprises at least one heating wire. Alternative heating elements can be provided, such as ceramic heaters, or fiber or mesh material heaters. Nonresistance heating elements such as sonic, piezo and jet spray may also be used in the atomizer in place of the heating wire.

According to an embodiment, the heating element comprises a plurality of heating wires, each of these heating wires being adapted to be operated selectively.

According to an embodiment, the atomizer, in order to be operated by the power supply, is connected to the power supply by means of a contact-type connection, e.g. the atomizer is connected to the power supply via a flexible conductive wire.

According to an embodiment, the flexible conductive wire is at least partially enclosed by a floating tube that is connected to the atomizer and that is adapted to float on the liquid surface.

According to an embodiment, in case the atomizer is connected to the power supply by means of a contact-type connection, the atomizer can include conductive contacting elements on an outer surface. The contacting elements are configured, when the atomizer floats on the liquid surface, irrespective of the current level of the fluid, to be guided by conductive guiding elements that are provided in the liquid reservoir and that are conductively connected to the power supply. While being guided by the guiding elements, the contacting elements are loosely conductively coupled to the guiding elements, and thus to the power supply.

The conductive contacting elements can e.g. be provided in the form of conductive wire brushes that are guided by conductive guiding elements in the form of conductive guiding troughs. Alternatively, the conductive contacting elements can e.g. be provided in the form of conductive loops that are guided by conductive guiding elements in the form of conductive guide wires.

According to an embodiment, the atomizer, in order to be operated by the power supply, is connected to the power supply by means of a noncontact-type connection. The atomizer can e.g. be adapted to be connected to the power supply via inductive coupling.

Typically, the atomizer is wickless. However, the atomizer can also comprise a wick to draw the liquid towards the atomizer.

According to an embodiment, the electronic vaping device is adapted to be simultaneously used by multiple users. In this case, the atomizer is adapted to be operated depending on the number of users simultaneously using the electronic vaping device.

According to another embodiment, the electronic vaping device is adapted to be simultaneously used by multiple users and comprises a plurality of atomizers. Each of these atomizers is assigned to one of the potential multiple users and is adapted to be operated when the respectively assigned user uses the electronic vaping device.

According to another aspect, an atomizer for an electronic vaping device is provided. The atomizer is adapted to atomize liquid stored in a liquid reservoir of the electronic vaping device when operated by a power supply of the electronic vaping device. The atomizer is particularly adapted to float on the surface of the liquid in the liquid reservoir.

Various embodiments of such an atomizer can be provided, as described above with respect to the atomizer of the electronic vaping device according to the first aspect.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS 10, 110, 210, 310, 410 electronic vaping device
12 power supply portion
14 atomizer/liquid reservoir portion
16 tapering end portion
18 battery
20 control electronics
24, 24a, 24b, 24c airflow sensor
28, 128, 228, 328, 428, 528 atomizer
32, 32a, 32b, 32c, 132a, 132b, 232a, 232b floating element
34a, 34b antenna coil
36, 36a, 36b, 36c heating wire
38 distance element
40, 40a, 40b, 40c contact port
44, 44a, 44b, 44c conductive wire
46 floating tube
48 liquid reservoir
50 vaping chamber
52 liquid surface
54, 54a, 54b, 54c opening
56, 56a, 56b, 56c air inhalation port
58 flexible tube
59, 59a, 59b, 59c, 159 mouthpiece
60 air inlets
62 wire brush
64 guide trough
66 loop
68 guide wire
136 heating element

The invention claimed is:

1. An electronic vaping device comprising:
a power supply portion including a power supply,
an atomizer/liquid reservoir portion including a liquid reservoir storing a liquid, and
an atomizer is configured and arranged to float on the surface of the liquid in the liquid reservoir and atomize the liquid stored in the liquid reservoir when operated by the power supply,
wherein the atomizer includes, at opposing inner surfaces, conductive guide troughs extending along a longitudinal direction of the atomizer/liquid reservoir, the conductive guide troughs configured and arranged to electrically couple the atomizer to the power supply.

2. The electronic vaping device of claim 1, wherein the atomizer further includes wire brushes configured and arranged to loosely contact the conductive guide troughs, and wherein the wire brushes and conductive guide troughs are configured and arranged to maintain electrical coupling between a heating wires of the atomizer and power supply irrespective of the fluid level within the atomizer/liquid reservoir.

3. An atomizer for an electronic vaping device,
wherein the atomizer is configured and arranged to atomize liquid stored in a liquid reservoir of the electronic vaping device when operated by a power supply of the electronic vaping device by receiving an electrical current from a power supply and heating a portion of the liquid in close proximity to the atomizer until vaporizing,
the atomizer including conductive wire brushes on an outer surface of the atomizer, the conductive wire brushes configured and arranged to facilitate electrically coupling the atomizer to the power supply, and
wherein the atomizer is further configured and arranged to float on the surface of the liquid in the liquid reservoir.

4. The atomizer of claim 3,
wherein the conductive wire brushes are configured and arranged to be conductively connected to the power supply via conductive guiding troughs.

5. An electronic vaping device comprising:
a power supply portion including
a power supply,
an atomizer/liquid reservoir portion including a liquid reservoir storing a liquid, and
an atomizer configured and arranged to atomize the liquid stored in the liquid reservoir when operated by the power supply, and to float on the surface of the liquid in the atomizer/liquid reservoir;
wherein the atomizer is electrically coupled to the power supply by conductive wire brushes on an outer surface of the atomizer and
conductive guiding troughs.

* * * * *